United States Patent [19]
Russell et al.

[11] Patent Number: 5,827,852
[45] Date of Patent: Oct. 27, 1998

[54] COATED PHARMACEUTICAL COMPOSITIONS

[75] Inventors: Carmelita Macklin Russell; Allen I. Dines, both of Cincinnati; James Grigg Upson, Springdale, all of Ohio

[73] Assignee: The Procter & Gamble Company, Cincinnati, Ohio

[21] Appl. No.: 307,537

[22] Filed: Sep. 16, 1994

Related U.S. Application Data

[63] Continuation of Ser. No. 204,791, Mar. 2, 1994, abandoned, which is a continuation of Ser. No. 56,701, Apr. 30, 1993, abandoned.

[51] Int. Cl.$^6$ ..................... A61K 31/495; A61K 31/435; A61K 31/44; A61K 31/19
[52] U.S. Cl. .................. 514/255; 514/256; 514/277; 514/290; 514/315; 514/325; 514/336; 514/568; 514/570; 514/613; 514/715; 424/463; 424/475
[58] Field of Search ..................... 424/456, 463, 424/475; 514/255, 256, 277, 290, 315, 325, 336, 568, 570, 613, 715

[56] References Cited

U.S. PATENT DOCUMENTS

| | | | |
|---|---|---|---|
| 3,515,781 | 6/1970 | Steinberg | 424/456 |
| 3,991,178 | 11/1976 | Humbert et al. | 424/54 |
| 4,136,163 | 1/1979 | Watson et al. | 424/54 |
| 4,230,688 | 10/1980 | Rowsell et al. | 514/613 |
| 4,459,425 | 7/1984 | Amano et al. | 514/715 |
| 5,098,715 | 3/1992 | McCabe et al. | 424/479 |

FOREIGN PATENT DOCUMENTS

| | | |
|---|---|---|
| 310299 | 4/1989 | European Pat. Off. . |
| 2577922 | 2/1985 | France . |

OTHER PUBLICATIONS

Jabloner et al., "A Molecular Approach to Flavor Synthesis, I. Menthol Esters of Varying Size and Polarity", J. Polym. Sci., Polym. Chem. Ed., 18(10), pp. 2933–2940 (1980).
Chemical Abstract Service, Abstract No. 88:11744p (1978).
Chemical Abstract Service, Abstract No. 103(2):11234a (1985).
Chemical Abstract Service, Abstract No. 107(8):64668j (1987).
Chemical Abstract Service, Abstract No. 108(2):11014g (1987).
Chemical Abstract Service, Abstract No. 110(16):141301a (1988).
Chemical Abstract Service, Abstract No. 110(18):160412d (1988).
U.S. application No. 07/955,013, Upson et al., filed Oct. 9, 1992.
U.S. application No. 07/887,128, Upson et al., filed May 20, 1992.
U.S. application No. 07/874,663, Upson et al., filed Apr. 27, 1992.
U.S. application No. 07/927,249, Court et al., filed Aug. 7, 1992.

*Primary Examiner*—Raymond Henley, III
*Attorney, Agent, or Firm*—Douglas C. Mohl; Loy M. White; T. David Reed

[57] ABSTRACT

Pharmaceutical composition suitable for coating comprising a composition for oral administration in unit dosage form wherein said composition has been coated with from about 0.01% to about 10% by weight of the composition with a volatile aromatic compound selected from the group consisting of 3-1-menthoxy propane-1,2-diol, N-substituted-p-menthane-3-carboxamides and acyclic carboxamides and mixtures thereof.

13 Claims, No Drawings

COATED PHARMACEUTICAL COMPOSITIONS

This is a continuation of application Ser. No. 08/204,791, filed on Mar. 2, 1994, now abandoned, which is a continuation of application Ser. No. 08/056,701, filed on Apr. 30, 1993, now abandoned.

TECHNICAL FIELD

The present invention relates to pharmaceutical compositions for oral administration coated with one or more volatile aromatics selected from the group consisting of 3-1-menthoxy propane-1,2-diol, N-substituted-p-menthane-3-carboxamides and acyclic carboxamides and mixtures thereof.

BACKGROUND OF THE INVENTION

The common cold, although not usually a serious illness, is a highly prevalent, discomforting and annoying infliction. The term common cold is applied to minor respiratory illnesses caused by a variety of different respiratory viruses. While rhinoviruses are the major known cause of common colds, accounting for approximately 30 percent of colds in adults, viruses in several other groups are also important. While immune responses occur, and infection with some respiratory tract viruses therefore could be prevented by a vaccine, development of a polytypic vaccine to cover all possible agents is impractical. Thus, the problem of controlling acute upper respiratory disease presents complex challenges, and the long-desired discovery of a single cure for the common cold is an unrealistic expectation.

Typical symptoms of the common cold are mild malaise, sore throat and nasal complaints. Nasal discharge, nasal congestion and/or sneezing frequently are present. Also common are sore, dry or scratchy throat and hoarseness and cough. Other symptoms may include mild burning of the eyes, loss of smell and taste, a feeling of pressure or fullness in the sinuses or ears, headache, and vocal impairment. Flu symptoms are similar but usually of greater severity, including fever, generalized aches and pains, fatigue and weakness, and chest discomfort. Allergy symptoms are more akin to the common cold, with more frequent/severe sinus pressure, drainage and headaches.

Pharmaceutical compositions safe and effective for treating colds, flu, and allergies are well known. Over-the-counter medications provide symptomatic relief of such illnesses. At present, only symptomatic treatment is available for the common cold; the majority of these drugs are taken orally. Exemplary prior art oral compositions for treatment of nasal and other cold, flu, allergy and sinus symptoms and the discomfort, pain, fever and general malaise associated therewith generally contain an analgesic (aspirin or acetaminophen) and one or more antihistamines, decongestants, cough suppressants, antitussives and expectorants. Other specific pharmaceutical actives for nasal symptoms (e.g., congestion) generally contain either oxymetazoline or phenylephrine. These actives are generally delivered topically to the nasal mucosa via a nasal spray. For individuals with certain medical conditions such as heart disease, hypertension, diabetes or thyroid disorders, oral drugs such as decongestants could pose a risk of unfavorable drug interactions and may cause an adverse reaction. It would, therefore, be highly desirable to deliver relief from specific nasal symptoms via compositions without the need for such pharmaceutical actives.

Nasal delivery of therapeutic agents has been well known for a number of years. See, for example, U.S. Pat. No. 4,749,700 to Wenig, issued Jun. 7, 1988, U.S. Pat. No. 4,778,810 to Wenig, et al., issued Oct. 18, 1988 and U.S. Pat. No. 4,729,997 to Wenig issued Mar. 8, 1988. Menthol has been administered orally from lozenges and the like as well as delivered to the nasal mucosa from an inhaler containing a wick and no other excipients, see, for example, Clinical Otolaryngology, 1988, vol. 13, pps. 25–29.

Coated pharmaceutical compositions have also been used to provide improved aesthetics, taste- and/or odor-masking and to provide flavoring and fragrances to tablets and the like, see, for example, U.S. Pat. No. 5,089,715 to McCabe et al., issued Mar. 24, 1992.

It has been discovered that oral pharmaceutical compositions coated with one or more of a volatile aromatic compound selected from the group consisting of 3-1-menthoxy propane-1,2-diol, N-substituted-p-menthane-3-carboxamides and acyclic carboxamides thereof provide the user with improved actual and/or perceived relief from nasal symptoms such as congestion and the like as well as sore throat and the like. In addition, such compositions will not cause drowsiness or other side effects attendant with oral decongestants.

Prior art formulations for treating cough, cold, cold-like, allergy and/or flu symptoms and the discomfort, pain, fever and general malaise associated therewith typically contain one or more of the pharmaceutical actives which are analgesics, anesthetics, antihistamines, decongestants, cough suppressants, antitussives and expectorants.

It is an object of the present invention to provide compositions and methods useful for treating cough, cold, cold-like, allergy and flu symptoms in humans and lower animals in need of such treatment. Another object is to provide such compositions and methods having improved actual and/or perceived benefits, e.g., speed of relief and/or duration of relief, and/or improved aesthetics.

These and other objects of the present invention will become readily apparent from the detailed description which follows.

SUMMARY OF THE INVENTION

The present invention is directed to pharmaceutical compositions suitable for coating comprising a composition for oral administration in unit dosage form wherein said composition has been coated with from about 0.01% to about 10% by weight of the composition with a volatile aromatic compound selected from the group consisting of 3-1-menthoxy propane-1,2-diol, N-substituted-p-menthane-3-carboxamides and acyclic carboxamides and mixtures thereof.

The present invention is also directed to methods for treating cough, cold, cold-like, allergy, and flu symptoms in a human or lower animal, said method comprising administering these compositions to a human or lower animal in need of such treatment.

All percentages and ratios used herein are by weight, and all measurements are made at 25° C., unless otherwise specified.

DETAILED DESCRIPTION OF THE INVENTION

The present invention relates to pharmaceutical compositions suitable for coating comprising a composition for oral administration in unit dosage form wherein said composition has been coated with from about 0.01% to about 10% by weight of the composition with a volatile aromatic compound selected from the group consisting of 3-1-menthoxy propane-1,2-diol, N-substituted-p-menthane-3-carboxamides and acyclic carboxamides and mixtures thereof.

The components of the compositions according to the present invention, and representative amounts, as well as the present invention methods are described in detail as follows.

Volatile Aromatics

The pharmaceutical compositions of the present invention are coated with a coating comprising a volatile aromatic selected from the group consisting of 3-1-menthoxy propane-1,2-diol, N-substituted-p-menthane-3-carboxamides and acyclic carboxamides and mixtures thereof. While not to be limited by theory, it is believed that the benefits obtained by the use of these coolants in the compositions of the present invention are the result of the unique cooling profiles for these compounds.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutanamide which is commercially available as WS-23 from Wilkinson Sword Limited.

Preferred for use herein is a mixture of 3-1-menthoxy propane 1,2-diol and N-ethyl-p-menthane-3-carboxamide in a ratio of about 3:1. The most preferred coating comprises a mixture of 3-1-menthoxy propane 1,2-diol, N-ethyl-p-menthane-3-carboxamide and N,2,3-trimethyl-2-isopropylbutanamide in a ratio of 2:1:1, respectively.

These volatile aromatic compounds are present at a level of from about 0.001% to about 10%, preferably at from about 0.001% to about 5%, more preferably from about 0.001% to about 0.5% by weight of the pharmaceutical compositions of the present invention. These volatile aromatic materials can be applied directly to the compositions of the present invention, or incorporated into a pharmaceutically-acceptable coating as described below.

Pharmaceutically-Acceptable Dosage Form

Various oral dosage forms suitable for coating can be used, including such solid forms as tablets, capsules, pills and lozenges. These oral forms can contain a safe and effective amount of a pharmaceutical active component. Solid oral dosage forms preferably comprise from about 0.1% to about 99%, more preferably from about 25% to about 99%, and most preferably from about 50% to about 99% of a pharmaceutical active component.

These dosage forms contain compatible solid or liquid filler diluents or encapsulating substances which are suitable for oral administration to a human or lower animal. The term "compatible", as used herein, means that the components of the compositions of the present invention are capable of being commingled with the pharmaceutical active, and with each other, in a manner such that there is no interaction which would substantially reduce the pharmaceutical efficacy of the compositions under ordinary use situations. Pharmaceutically-acceptable carrier materials must, of course, be of sufficiently high purity and sufficiently low toxicity to render them suitable for administration to the human being treated. Preferably the present invention compositions comprise from about 0.1% to about 99.99% of one or more pharmaceutically-acceptable carrier materials.

Tablets can be compressed, molded, triturated, enteric-coated, sugar-coated, film-coated or multiple compressed, containing suitable binders, lubricants, diluents, disintegrating agents, coloring agents, flavoring agents, preservatives and flow-inducing agents.

Techniques and compositions for making solid oral dosage forms are described in Marshall, "Solid Oral Dosage Forms," *Modern Pharmaceutics*. Vol. 7, (Banker and Rhodes, editors), 359–427 (1979), incorporated by reference herein. Techniques and compositions for making tablets (compressed and molded), capsules (hard and soft gelatin) and pills are described in *Remington's Pharmaceutical Sciences* (Arthur Osol, editor), 1553–1593 (1980), incorporated herein by reference. Specific examples of pharmaceutically acceptable carriers and excipients that may be used to formulate oral dosage forms, are described in U.S. Pat. No. 3,903,297, Robert, issued Sep. 2, 1975, incorporated by reference herein.

Also useful are soft and hard gelatin capsules wherein the shell is either coated, or alternatively, the volatile aromatic compound is contained within the shell material. Preferably, the gelatin shell is essentially transparent so as to enhance the aesthetic qualities of the capsule. Soft and hard gelatin shells generally comprise gelatin, a plasticizer and water. The starting gelatin material generally used in the manufacture of these capsules is obtained by the partial hydrolysis of collagenous material. Gelatin suitable for capsule manufacture is commercially available from the Sigma Chemical Company, St. Louis, Mo. For a general description of gelatin and gelatin-based capsules, see *Remington's Pharmaceutical Sciences*, 16th ed., Mack Publishing Company, Easton, Pa. (1980), page 1245 and pages 1576–1582; and U.S. Pat. No. 4,935,243, to Borkan et al., issued Jun. 19, 1990; these two references being incorporated herein by reference in their entirety.

One or more plasticizers is incorporated to produce a gelatin shell. Useful plasticizers of the present invention include glycerin, sorbitan, sorbitol, or similar low molecular weight polyols, and mixtures thereof.

The gelatin shells of the instant invention can be prepared by combining appropriate amounts of gelatin, water, plasticizer, and any optional components in a suitable vessel and agitating and/or stirring while heating to about 65° C. until a uniform solution is obtained. Hard gel capsules can then be used for encapuslating the desired quantity of fill material employing methods known to the skilled artisan. Soft gelatin shell compositions containing the desired quantity of the fill composition are made by employing standard encapsulation methodology to produce one-piece, hermetically sealed, soft gelatin capsules.

The gelatin capsules are formed into the desired shape and size so that they can be readily swallowed. The gelatin capsules of the instant invention are of a suitable size for easy swallowing and typically contain from about 100 mg to about 2000 mg of the pharmaceutical active composition. The coolant can be added either as a seperate coating applied directly to the gelatin capsule, or it can be incorporated into the gelatin capsule shell itself without the need for a seperate coating step. Gelatin capsules and encapsulation methods are described in P. K. Wilkinson et al., "Softgels: Manufacturing Considerations", *Drugs and the Pharmaceutical Sciences,* 41 (*Specialized Drug Delivery Systems*), P. Tyle, Ed. (Marcel Dekker, Inc., New York, 1990) pp. 409–449; F. S. Hom et al., "Capsules, Soft", *Encyclopedia of Pharmaceutical Technology,* vol. 2, J. Swarbrick and J. C. Boylan, eds. (Marcel Dekker, Inc., New York, 1990) pp. 269–284; M. S. Patel et al., "Advances in Softgel Formulation Technology", *Manufacturing Chemist,* vol. 60, no. 7, pp. 26–28 (July 1989); M. S. Patel et al., "Softgel Technology", *Manufacturing Chemist,* vol. 60, no. 8, pp. 47–49 (August 1989); R. F. Jimerson, "Softgel (Soft Gelatin Capsule) Update", *Drug Development and Industrial Pharmacy* (*Interphex '86 Conference*), vol. 12, no. 8 & 9, pp. 1133–1144 (1986); and W. R. Ebert, "Soft Elastic Gelatin Capsules: A Unique Dosage Form", *Pharmaceutical Technology,* vol. 1, no. 5, pp. 44–50 (1977); these references are incorporated by reference herein in their entirety.

Other optional ingredients well known to the pharmacist's art may also be included in amounts generally known for these ingredients, for example, natural or artificial sweeteners, flavoring agents, colorants and the like to provide a palatable and pleasant looking final product, antioxidants, for example, butylated hydroxy anisole or butylated hydroxy toluene, and preservatives, for example, methyl or propyl paraben, potassium sorbate, or sodium benzoate, to prolong and enhance shelf life. A preferred optional component is also caffeine.

Pharmaceutical Actives

The pharmaceutical compositions according to the present invention optionally comprise a safe and effective amount of a pharmaceutical active, preferably a pharmaceutical colds actives useful for treating cough, cold, cold-like, allergy and/or flu symptoms. Such pharmaceutical actives are well known, and are generally recognized as being an active having analgesic, anti-inflammatory, anesthetic, antihistamine, decongestant, cough suppressant, demulcents, antitussive, and/or expectorant properties.

The phrase "safe and effective amount", as used herein, means an amount of a compound or composition high enough when administered orally to significantly positively modify the condition to be treated, but low enough to avoid serious side effects (at a reasonable benefit/risk ratio), within the scope of sound medical judgment. The safe and effective amount of the pharmaceutical active will vary with the particular condition being treated, the age and physical condition of the patient being treated, the severity of the condition, the duration of the treatment, the nature of concurrent therapy, the specific pharmaceutical active employed, the particular pharmaceutically-acceptable carrier utilized, and like factors within the knowledge and expertise of the attending physician. Typically, the pharmaceutical active(s) comprise from about 0.001% to about 99.9%, by weight, of the pharmaceutical compositions of the present invention, preferably from about 0.001% to about 75%, and most preferably from about 0.01% to about 30%.

Examples of actives commonly utilized in cough/cold preparations are, for example, a decongestant such as pseudoephedrine, phenylpropanolamine, phenylephrine and ephedrine, their pharmaceutically acceptable salts; an antitussive such as dextromethorphan, chlophedianol, carbetapentane, caramiphen, noscapine, diphenhydramine, codeine, menthol, hydrocodone, hydromorphone, fominoben, their pharmaceutically-acceptable salts; an expectorant or mucolytic such as glyceryl guaiacolate, terpin hydrate, ammonium chloride, N-acetylcysteine and bromhexine, ambroxol, their pharmaceutically acceptable salts; and an antihistamine such as chlorpheniramine, brompheniramine, dexchlorpheniramine, dexbromphreniramine, triprolidine, azatadine, doxylamine, tripelennamine, cyproheptadine, hydroxyzine, clemastine, carbinoxamine, phenindamine, bromodiphenhydramine, pyrilamine, their pharmaceutically acceptable salts, as well as the non-sedating antihistamines which include acrivastine, AHR-11325, astemizole, azelastine, cetirizine, ebastine, ketotifen, lodoxamide, loratidine, levocabastine, mequitazine, oxatomide, setastine, tazifylline, temelastine, and terfenadine, their pharmaceutically acceptable salts: all of these components, as well as their acceptable dosage ranges are described in the following: U.S. Pat. No. 4,783,465 to Sunshine et al., issued Nov. 8, 1988, U.S. Pat. No. 4,619,934 to Sunshine et al., issued Oct. 28, 1986, which are incorporated by reference herein. Also useful are bronchodilators such as terbutaline, atropine, aminophylline, epinephrine, isoprenaline, metaproterenol, bitoterol, theophylline and albuterol. Also used are analgesic compounds such as aspirin, acetaminophen, ibuprofen, and naproxen; and topical anesthetics/analgesics such as phenol, benzocaine, hexyl resorcinol, and dyclonine.

Other preferred pharmaceutical actives include ingestible pharmaceutical agents effective for treating the gastrointestinal tract (e.g., symptoms such as heartburn, stomachache and indigestion), such as bismuth-containing agents and $H_2$ receptor-blocking anti-secretory agents. Preferred antacid agents have stomach acid neutralizing capacities, such as those agents selected from the group consisting of: aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucralfate, and mixtures thereof. Bismuth-containing agents include, for example, bismuth subsalicylate, bismuth aluminate, bismuth citrate, bismuth subcitrate, bismuth nitrate, bismuth subcarbonate, bismuth subgalate, and mixtures thereof. A particularly preferred bismuth salt is bismuth subsalicylate. Examples of $H_2$ receptor-blocking anti-secretory agents include ranitidine and cimetidine. Preferred antacid agents for use herein are aluminum hydroxide, magnesium hydroxide, dihydroxy aluminum sodium carbonate, calcium carbonate, and mixtures thereof. Most preferred is calcium carbonate.

Other pharmaceutical actives useful in the present invention calcium channel blockers, beta-blockers, antibacterials, antidepressants, antidiabetics, anti-emetics, cerebral stimulants, sedatives, anti-parasitics, diuretics, muscle relaxants, anti-Parkinsonian agents, bronchodilators, cardiotonics, antibiotics, antivirals, nutritional supplements (such as vitamins, minerals, fatty acids, amino acids, and the like), and mixtures thereof.

For solid dosage forms, the volatile aromatic coolants of the present invention are applied directly to the surface of the dosage form alone, or preferably by being incorporated into any conventional pharmaceutically-acceptable coating. Suitable coating techniques are described in *Remington's Pharmaceutical Sciences,* 17th ed., Mack Publishing Company, Easton, Pa. (1985), pages 1233–43, this reference being incorporated herein by reference. The preferred film coating of this invention is comprised of a commercial film-coating product designed for aqueous film coating containing a water-soluble, film-forming resin, hydroxypropyl methylcellulose and polyethylene glycol (or other suitable plasticizing agents such as propylene glycol or glycerin) and optionally containing titanium dioxide (or other colorant or opacifying agent). Such a product is commercially available under the trade name Opadry White™ (Colorcon, West Point, Pa.). A suitable blend comprises 0 to about 20% w/w titanium dioxide or colorant, about 5 to about 95% w/w hydroxypropyl methylcellulose, and 0 to about 25% w/w polyethylene glycol. The most preferred embodiment comprises 10.5% non-water additives, of which 7.5% is Opadry. Therefore, most of the weight of the non-water additives of the coating dispersion is comprised of Opadry. More than 25% Opadry makes the coating too thick to spray easily while concentrations that are too low decrease the efficiency of coating. This blend plus flavoring and sweetening agents is added to purified water at ambient temperature in a vortex mixer such as a Lightnin Mixer Model V-7 (Mixing Equipment Co., Rochester, N.Y.). Other Opadry coating products such as Opadry Clear or Opadry with various pigment lakes may also be used in the invention to change the appearance of the tablets without adversely affecting the flavor characteristics of the invention. Other aqueous film-forming polymers may also be employed in place of hydroxypropyl methylcellulose.

Method of Treatment

The present invention also relates to a method for treating cough, cold, cold-like, allergy and flu symptoms in a human or lower animal. Said method comprises administering to a human or lower animal in need of such treatment the compositions of the present invention.

The following examples further describe and demonstrate embodiments within the scope of the present invention. These examples are given solely for the purpose of illustration and are not to be construed as a limitation of the present invention as many variations thereof are possible without departing from the spirit and scope.

EXAMPLE I

A coated tablet composition for oral administration is prepared by combining the following ingredients:

| Ingredients | mg |
|---|---|
| Tablet: | |
| Acetaminophen | 500.0 |
| Pseudoephedrine | 30.0 |
| Povidone | 37.5 |
| Lactose | 102.9 |
| Alcohol | qs* |
| Stearic Acid | 15.0 |
| Talc | 22.5 |
| Corn Starch | 71.2 |
| Coating | |
| 3-1-menthoxy propane-1,2-diol | 1.5 |
| Alcohol | 4.0 |
| Hydroxypropyl Methylcellulose | 8.5 |
| Water | 86.0 |

*Not part of the final tablet or caplet

The acetaminophen, povidone and lactose are blended together. The alcohol is added slowly and mixed well. The wet mass is screened through a #4 mesh screen. The granulation is dried at 50° C. overnight and then sized through a #20 mesh screen. The remaining ingredients are bolted through a #60 mesh screen. The two granulations are mixed and then compressed into tablets using conventional tableting equipment known to those skilled in the art. The tablets are then pan coated with the coating mixture using conventional coating equipment.

Administration of 1 or 2 of the above tablets to a human in need of treatment provides improved relief from cough, cold-like, flu and flu-like symptoms.

EXAMPLE II

A coated hard gelatin capsule composition for oral administration is prepared by combining the following ingredients:

| Ingredients | Amount |
|---|---|
| Capsule: | |
| Ibuprofen | 100 mg |
| Pseudoephedrine HCl | 30 mg |
| Astemizole | 5 mg |
| Glyceryl guaiacolate | 100 mg |
| Coating: | |
| 3-1-menthoxy propane-1,2-diol | 0.750 |
| N-ethyl-p-menthane-3-carboxamide | 0.375 |
| N, 2,3-trimethyl-2-isopropylbutanamide | 0.375 |
| Hydroxypropyl Methylcellulose | 8.500 |
| Alcohol | 4.000 |
| Water | 86.000 |

Triturate active ingredients and q.s. with lactose to selected capsule size. The capsules are then coated with the coolant mixture as described above in Example I.

Administration of 1 or 2 of the above capsules to a human in need of treatment provides improved relief from cough, cold-like, flu and flu-like symptoms.

EXAMPLE III

A soft gelatin capsule for oral administration is prepared by combining the following ingredients:

| Ingredient | W/W % |
|---|---|
| Solubilized Fill: | |
| Polyvinylpyrrolidone 12pf[1] | 150.00 |
| Polyethylene Glycol 600 | 200.00 |
| Ibuprofen | 200.00 |
| Pseudoephedrine HCl | 30.00 |
| Water | 40.00 |
| Ammonium hydroxide 30% | 3.00 |
| Soft Gelatin Coating: | |
| Gelatin | 47.00 |
| Glycerin | 15.00 |
| Water | Q.S. |
| 3-1-menthoxy propane-1,2-diol | 1.5 |

[1]Available as Kollidon ® 12pf, from BASF, Parsippany, NJ, 07054.

The fill ingredients are combined in a suitable vessel and heated with mixing at about 65° C. to form a uniform solution. The soft gelatin ingredients are combined and heated to about 65° C. to form a uniform mixture. Using standard encapsulation methodology, the resulting solution is used to prepare soft gelatin capsules containing approximately 623 mg of the fill material wherein the volatile aromatic is incorporated into the soft gelatin capsule shell.

The resulting soft gelatin capsules are suitable for oral administration.

What is claimed is:

1. An oral composition comprising:
   a) a pharmaceutical active in a unit dosage form suitable for coating; and
   b) a coating comprising a pharmaceutically-acceptable coating material and from about 0.01% to about 10% by weight of a volatile aromatic compound selected from the group consisting of 3-1-menthoxy propane-1,2-diol, N-substituted-p-menthane-3-carboxamides, acyclic carboxamides, and mixtures thereof.

2. The composition of claim 1 wherein said composition comprises a mixture of 3-1-menthoxy propane-1,2-diol and N-ethyl-p-menthane-3-carboxamide.

3. The composition of claim 2 wherein said composition comprises a mixture of 3-1-menthoxy propane-1,2-diol and N-ethyl-p-menthane-3-carboxamide in a weight ratio of about 3:1, respectfully.

4. The composition of claim 1 wherein said composition comprises a mixture of 3-1-menthoxy propane-1,2-diol, N-ethyl-p-menthane-3-carboxamide and N, 2,3-trimethyl-2-isopropylbutanamide.

5. The composition of claim 4 wherein said composition comprises a mixture of 3-1-menthoxy propane-1,2-diol, N-ethyl-p-menthane-3-carboxamide and N, 2,3-trimethyl-2-isopropylbutanamide in a weight ratio of about 2:1:1, respectively.

6. The pharmaceutical composition of claim 1 wherein said pharmaceutical active is a colds active selected from the group consisting of analgesics, anti-inflammatories, anesthetics, antihistamines, decongestants, cough suppressants, demulcents, antitussives, expectorants, and mixtures thereof.

7. The pharmaceutical composition according to claim 6 wherein the pharmaceutical active is selected from the group consisting of pseudoephedrine, phenylpropanolamine, phenylephrine, ephedrine, dextromethorphan, chlophedianol, carbetapentane, caramiphen, noscapine, diphenhydramine, codeine, menthol, hydrocodone, hydromorphone, fominoben, glyceryl guaiacolate, terpin hydrate, ammonium chloride, N-acetylcysteine and bromhexine, ambroxol, chlorpheniramine, brompheniramine, dexchlorpheniramine, dexbromphreniramine, triprolidine, azatadine, doxylamine, tripelennamine, cyproheptadine, hydroxyzine, clemastine, carbinoxamine, phenindamine, bromodiphenhydramine, pyrilamine, acrivastine, AHR-11325, astemizole, azelastine, cetirizine, ebastine, ketotifen, lodoxamide, loratidine, levocabastine, mequitazine, oxatomide, setastine, tazifylline, temelastine, terfenadine, terbutaline, atropine, aminophylline, epinephrine, isoprenaline, metaproterenol, bitoterol, theophylline, albuterol, aspirin, acetaminophen, ibuprofen, naproxen, phenol, benzocaine, hexyl resorcinol, dyclonine, the pharmaceutically acceptable salts thereof, and mixtures thereof.

8. A pharmaceutical composition according to claim 1 wherein the composition is in a unit dosage form selected from the group consisting of tablets, capsules, pills, and lozenges.

9. A pharmaceutical composition according to claim 8 wherein the composition is in the form of a capsule selected from the group consisting hard gelatin capsules and soft gelatin capsules.

10. A pharmaceutical composition according to claim 9 wherein the composition is a soft gelatin capsule.

11. A method for treating cough, cold, cold-like, allergy, and flu symptoms in a human or lower animal, said method comprising administering to a human or lower animal in need of such treatment the composition of claim 1.

12. A method for treating cough, cold, cold-like, allergy, and flu symptoms in a human or lower animal, said method comprising administering to a human or lower animal in need of such treatment the composition of claim 2.

13. A method for treating cough, cold, cold-like, allergy, and flu symptoms in a human or lower animal, said method comprising administering to a human or lower animal in need of such treatment the composition of claim 5.

* * * * *